United States Patent [19]

Relyveld

[11] Patent Number: 4,625,019

[45] Date of Patent: Nov. 25, 1986

[54] POLYMERIC PRODUCT OF DAUNORUBICIN AND GLUTARALDEHYDE

[75] Inventor: Edgar H. Relyveld, Paris, France

[73] Assignee: Institut Pasteur, Paris, France

[21] Appl. No.: 552,148

[22] PCT Filed: Feb. 25, 1983

[86] PCT No.: PCT/FR83/00036

§ 371 Date: Oct. 26, 1983

§ 102(e) Date: Oct. 26, 1983

[87] PCT Pub. No.: WO83/02946

PCT Pub. Date: Sep. 1, 1983

[30] Foreign Application Priority Data

Feb. 26, 1982 [FR] France .................................. 82 03272

[51] Int. Cl.$^4$ ............................................. C07H 15/24
[52] U.S. Cl. ..................................................... 536/6.4
[58] Field of Search ........................ 536/6.4; 424/180; 514/34

[56] References Cited

U.S. PATENT DOCUMENTS 4,149,003  4/1979  Carlsson et al. .
4,202,967  5/1980  Tong et al. ........................... 424/180

FOREIGN PATENT DOCUMENTS 0004467  3/1979  European Pat. Off. .
2382450  3/1978  France .

OTHER PUBLICATIONS

A. Bernstein et al., J. Natl. Cancer Inst. 1978, 60, 379-384.
E. Hurwitz, M. Wilchek and J. Pitha, Soluble Macromolecules as Carriers for Daunorubicin, J. Appl. Biochem. 2,25-35 (1980).
Sjur Olsnes, "Directing Toxins to Cancer Cells", in Nature, vol. 290, 84, Mar. 12, 1981.
Jung-Yaw Lin, et al, "Lectin Derivatives of Methotrexate and Chlorambucil as Chemotherapeutic Agents", JNCI, vol. 66, No. 3, Mar. 1981.
T. Kato et al, JAMA 1981, 245, 1123-1127, Arterial Chemoembolization with Microcapsules Containing an Anticancer Agent.
H. E. Blythman et al, "Antibody Carriers for Toxins or Anticancer Agents", NATURE 1981, 290, 145-146.
E. Hurwitz et al., Europ. J. Cancer 1978, 14, 1213-1220.
"The Use of Implantable Pumps" (JAMA 1981, 246, 925-926).
Pierce Chemical Company published in 1981, vol. 2, entitled "Pierce Bioresearch Products Technical Bulletin—Double-Agents Bifunctional Crosslinking Reagents".

Primary Examiner—Johnnie R. Brown
Assistant Examiner—Elli Peselev
Attorney, Agent, or Firm—Burns, Doane, Swecker & Mathis

[57] ABSTRACT

According to the invention, the antitumor agent such as daunorubicin and a well-defined quantity of a bifunctional crosslinking agent, such as glutaraldehyde, are brought together. A form of polymeric product is obtained, which is insoluble in aqueous media but which, on being resuspended in an aqueous medium in the absence of glutaraldehyde, gradually releases the antitumor agent in a soluble form, preserving its antitumor activity. Improvement of the conditions of treatment with antitumor agents.

1 Claim, No Drawings

POLYMERIC PRODUCT OF DAUNORUBICIN AND GLUTARALDEHYDE

BACKGROUND OF THE INVENTION

1. Field of the Invention

The invention relates to the province of antitumor agents. In the present description the expression "antitumor agents" is synonymous with the expression "cytostatic agents". The subject of the present invention is an improved form of presentation of such agents which enables them to be endowed with increased efficiency. The invention also relates to the preparation of new forms of presentation of the agents in question and, in general, a process for increasing the efficiency of use of antitumor agents or cytostatic agents.

2. Description of the Prior Art

It is known that the use of present antitumor agents raises many difficulties in practice. At doses which are high enough to be effective, such agents are extremely toxic. Their use is however justified by the seriousness of the illnesses which have to be combated. Furthermore, clinical treatment conditions are themselves far from being optimal because, in many cases, the active agents are very rapidly eliminated from the organism, so that they have to be administered more frequently, which further increases the toxicity hazards and, in any case, makes the treatment very uncomfortable for the patient.

In recent work, various attempts have been made to overcome these disadvantages, in particular by fixing the antitumor agent, for example daunomycin (or daunorubicin) on various soluble or insoluble supports. There may be mentioned in this connection the paper by A. Bernstein et al., J. Natl. Cancer Inst. 1978, 60, 379-384. The authors propose to fix daunomycin on dextran to improve antitumor efficiency. For the purpose of fixing, dextran, which is previously oxidized, is brought together with daunomycin and the combination is then reduced with sodium borohydride. The authors report a number of undesirable secondary effects at the time of the administration, as a result of the presence of the dextran as a supporting agent.

There may also be mentioned as a literature reference the paper by E. Hurwitz, M. Wilchek and J. Pitha, Soluble Macromolecules as Carriers for Daunorubicin., J. Appl. Biochem. 2,25-35 (1980). According to these authors, daunorubicin is fixed through its ketone group on soluble macromolecular hydrazides, in a reversible manner. The fixation takes place, consequently, by means of sulfide bonds. The difficulties which are met with are that the product no longer possesses its cytotoxic properties, or that the conjugated agent gradually becomes insoluble, which makes it unsuitable for administration.

The paper by Sjur Olsnes "Directing Toxins to Cancer Cells" in Nature, Vol. 290, Mar. 12, 1981, gives a good description of the problems involved in the administration of antitumor agents having very high toxicity. It refers to a number of techniques for trying to improve the conditions of administration, and in particular to permit a more direct action of the active agent on the cancerous cell by improving its selectivity. It is proposed, for example, to fix the antitumor agent on a toxin capable of acting directly on the cell.

There may also be mentioned the paper by Jung-Yaw Lin, Jiann-Shyong Li and Ta-Cheng Tung "Lectin Derivatives of Methotrexate and Chlorambucil as Chemotherapeutic Agents", JNCI, Vol. 66, No. 3, March 1981. The authors propose to fix the agents, by covalent bonding, on a lectin, so as to prepare a conjugated product whose efficiency is superior to the active agent employed separately.

In general, various processes are known, especially in recent years, which are intended for conveying the medications, retarding their elimination, reducing their toxicity, and, particularly, increasing their activity. These studies are, among others, the subject of a recent publication: Drug Carriers in Biology and Medicine, G. Gregoriadis (ed.) Academic Press 1979, which summarizes the results obtained with natural macromolecules, cells and synthetic compounds (such as the liposomes).

Other ways which have been the subject of recent publications are: arterial chemoembolization with microcapsules containing an anticancer agent (T. Kato et al., JAMA 1981, 245, 1123-1127), antibody carriers for toxins or anticancer agents (H. E. Blythman et al., NATURE 1981, 290, 145-146; S. Olsnes, NATURE 1981, 290, 84; E. Hurwitz et al., Europ. J. Cancer 1978, 14, 1213-1220), the use of implantable pumps (JAMA 1981, 246, 925-926).

The problems posed by the administration of antitumor agents or cytostatic agents are made particularly difficult by the nature of the illness and very high toxicity of the active product. The aim of the invention is generally to improve the efficiency of the use of antitumor agents, so as to allow their gradual release in the organism, which clearly improves their efficiency and the patient's comfort.

GENERAL DESCRIPTION OF THE INVENTION

The invention relates to antitumor agents with improved efficiency which are in an autopolymerized form after bringing together an effective quantity of a bifunctional crosslinking agent and at least one antitumor agent carrying groups capable of reacting with the crosslinking agent in question, the said quantity being capable of producing a product which is insoluble in aqueous media, which product, after elimination of any excess crosslinking agent, permits, when suspended in an aqueous medium, the active agent to be gradually released in a soluble form, preserving its antitumor activity.

As documents illustrating the prior art, there may be mentioned French Patent published under the No. 2,382,450 and European Patent Application published under the No. 0,004,467.

French Pat. No. 2,382,450 relates to a family of new pyridine derivatives, capable of being employed as bifunctional agents, particularly as substitutes for glutaraldehyde which is a well-known agent for this purpose. It relates to a particular category of bifunctional agents and contains no teaching of the preparation of antitumor products. Moreover, its description criticizes the efficiency of glutaraldehyde as a crosslinking agent. The person skilled in the art could thus expect to encounter some difficulties when using such an agent.

According to the present invention, glutaraldehyde is perfectly suitable for the preparation of antitumor products. European Patent Application published under the No. 0,004,467, in the name of the University of California describes a new form of presenting antitumor agents, such as daunorubicin and adriamycin, and provides for coupling two molecules of the base product to produce a dimer. The latter can be incorporated in a liposome, or presented in aqueous solution, which necessarily implies that these new dimer derivatives are soluble in aqueous media. It is well established in the University of California patent that the new compounds are bis-anthracyclins whose essential characteristic is that they consist of two anthracyclin units joined together by a crosslink.

A fundamental difference of the antitumor agents according to the invention, as opposed to the compounds which are the subject of the University of California patent, is that the said agents are products which are insoluble in aqueous media. The suspending in such a medium permits the active agent to be gradually released, while preserving its antitumor activity. The polymeric products according to the invention are insoluble in aqueous media. This property is particularly advantageous in human therapy. Being insoluble in aqueous media, the antitumor agent gradually depolymerizes on coming into contact with the body fluids, permitting the active product to redissolve so as to exert its effectiveness in full.

European Pat. No. 0,004,467 makes no disclosure of the characteristics or the properties of such antitumor products or of the means for obtaining them.

The preferred bifunctional crosslinking agent is glutaraldehyde. However, the invention is not limited to the use of glutaraldehyde and other agents can be employed, such as N-succinimidyl 3-(2-pyridyldithio)propionate (SPDP) or succinimidyl 4-(p-maleimidophenyl)butyrate (SMBP). The expert will find a list of bifunctional crosslinking agents which can also be used in accordance with the present invention in the bulletin of the PIERCE Chemical Company published in 1981, volume 2, entitled "Pierce Bioresearch Products Technical Bulletin—Double-Agents Bifunctional Crosslinking Reagents". The bulletin distributed by the Pierce Chemical Company, Box 117 Rockford, IL USA 61105 also contains a list of literature references giving the specifications and the respective characteristics of the crosslinking agents. The Pierce bulletin is introduced in the present description by way of reference and those skilled in the art can refer to it, if need be.

DESCRIPTION OF PREFERRED EMBODIMENT

In its preferred form, the invention relates to antitumor agents which are in an autopolymerized form after bringing together at least one antitumor agent carrying groups capable of reacting with an aldehyde, with an effective quantity of glutaraldehyde, the said quantity being capable of producing a product which is insoluble in aqueous media, which product, after elimination of any excess glutaraldehyde, permits, when placed in suspension in an aqueous medium, the active agent to be gradually released in a soluble form, preserving its antitumor activity.

It is also an object of the invention to provide a process for preparing new antitumor agents mentioned above, the said process consisting in bringing together the antitumor agent to be treated with an effective quantity of a bifunctional crosslinking agent, capable of reacting with the antitumor agent, and in recovering a product in an autopolymerized form insoluble in aqueous media, the said quantity of crosslinking agent being capable of producing a product which is insoluble in aqueous media, which product, after elimination of any excess crosslinking agent, permits, when placed in suspension in an aqueous medium, the active agent to be gradually released in a soluble form, preserving its antitumor activity.

In a preferred embodiment, the invention has as its object a process consisting in placing the antitumor agent to be treated in contact with an effective quantity of glutaraldehyde and in recovering a product in an autopolymerized form insoluble in aqueous media, the said agent to be treated carrying groups capable of reacting with an aldehyde and the said quantity of glutaraldehyde being capable of producing a product insoluble in aqueous media, which product, after elimination of any excess glutaraldehyde, permits, when placed in suspension in an aqueous medium, the active agent to be gradually released in a soluble form, preserving its antitumor activity.

In yet another embodiment, the invention relates to a process for improving the efficiency of use of antitumor agents, the said process consisting in placing the agent to be treated in contact with an effective quantity of a bifunctional crosslinking agent capable of reacting with the antitumor agent and in recovering a product in an autopolymerized form insoluble in aqueous media, the said quantity of crosslinking agent being capable of producing a product insoluble in aqueous media, which product, after elimination of any excess crosslinking agent, permits, when placed in suspension in an aqueous medium, the active agent to be gradually released in a soluble form, preserving its antitumor activity.

In a preferred embodiment, the invention relates to a process for improving the efficiency of use of antitumor agents carrying groups capable of reacting with aldehydes, the said process consisting in placing the agent to be treated in contact with an effective quantity of glutaraldehyde and in recovering a product in an autopolymerized form insoluble in aqueous media, the said quantity of glutaraldehyde being capable of producing a product insoluble in aqueous media, which product, after elimination of any excess glutaraldehyde, permits, when placed in suspension in an aqueous medium, the active agent to be gradually released in a soluble form, preserving its antitumor activity.

In all the abovementioned embodiments of the invention, it is essential that the crosslinking agent be capable of reacting with the antitumor agent to be treated. The latter's reactive groups will, naturally, depend on the nature of the crosslinking agent. The antitumor agent can, for example, comprise —$NH_2$ groups, epsilon amino groups of lysine residues, sulfhydryl groups of cysteine residues, and other similar reactive groups.

When glutaraldehyde is employed as the crosslinking agent, the invention can be applied to antitumor agents of a wide variety, provided they carry groups capable of reacting with aldehydes. These groups are for example reactive hydrogen atoms or —$NH_2$ groups.

As examples of specific antitumor agents, there may be mentioned daunorubicin, also called daunomycin (see Merck Index 1976 No. 2815) and similar derivatives, such as doxorubicin or adriamycin (Merck Index 1976 No. 3428). There may also be mentioned the products methotrexate (Merck Index 1976 No. 5858) and Mitomycin I (Merck Index 1976 No. 6060). Needless to say, these examples are only purely illustrative.

In the following description the invention will be illustrated with reference to the preferred crosslinking agent, namely glutaraldehyde, but it will be noted that, as mentioned already, numerous other bifunctional agents can also be employed as required by the invention.

According to a preferred embodiment of the invention, the antitumor agent to be treated is placed in contact with glutaraldehyde under well-defined conditions. As already mentioned, the antitumor agent must be of the type which is capable of reacting with glutaraldehyde aldehyde and more generally with any aldehyde. According to the prior art, and particularly in the papers referred to at the beginning of the present description, the fixation of antitumor agents on certain supports took place through organic reactions or through affinity. According to the present invention, the reaction with glutaraldehyde results in autopolymerization of the active agent. Within the meaning of the present description, the expression "autopolymerization" refers to an oligomeric or polymeric form of the initial tumor agent, a form which, in contrast to the starting agent, is insoluble in aqueous media, in particular the biological fluids or physiological solutions. The nature of the reactions involved in the prior art did not make it possible to arrive at such an autopolymerization.

The conditions for bringing the antitumor agent and glutaraldehyde together must not only lead to an insoluble autopolymerized product, but must also be such that, when the said product is then, in the absence of glutaraldehyde, suspended in an aqueous medium, it is capable of depolymerizing, releasing the active agent in a soluble form, while preserving its antitumor activity. The reaction conditions, and particularly the quantity of glutaraldehyde employed, must therefore be chosen so as to satisfy the abovementioned requirements. If an excess of glutaraldehyde is employed, the result is a saturation of the reactive groups of the antitumor agent which combine with the glutaraldehyde groups and the final products which is obtained is soluble in aqueous media. On the other hand, if too small a quantity of glutaraldehyde is employed, the latter is incapable of fixing all the reactive groups of all the molecules of the antitumor agent, so that there remain free molecules of this agent which have not reacted. Those skilled in the art will understand that the happy medium to be adopted for choosing the quantity of glutaraldehyde which is to be used will depend on the nature of the antitumor agent, in particular on the number of reactive groups which it possesses. Preliminary tests enable the optimum quantities of glutaraldehyde to be established, these quantities having to be intermediate between two extremes, on the one hand those which are excessive and lead to a product which is soluble in aqueous media and, on the other hand those which are inadequate and leave residual quantities of unreacted antitumor agent in the reaction medium.

It is also self-evident that the reaction time can play a part. The reaction between the antitumor agent and the glutaraldehyde must be followed until the above requirements are satisfied.

In the following examples, the reaction between glutaraldehyde and daunorubicin is illustrated. Three concentrations of glutaraldehyde have been tried, namely 0.027% by weight, 0.27% and 2.7% relative to the reaction medium which contained 1 mg/ml of daunorubicin. With contact times of 15 min. and 30 min. at ambient temperature, the reaction conditions which were suitable for the needs of the invention implied the use of glutaraldehyde concentrations of approximately 0.27%. At such a concentration, in fact, the quantity of autopolymerized product reached nearly 100%. At a glutaraldehyde concentration of 0.027%, on the other hand, the quantity of autopolymerized product was insufficient and there remained free unreacted daunorubicin. Similarly, at glutaraldehyde concentrations of 2.7% the quantity of product remaining soluble in the aqueous medium had become large, which was unsatisfactory.

The preceding indications are given to those skilled in the art who will be able, in each particular case, using preliminary tests, to define optimum conditions for the reaction according to the invention between the antitumor agent and glutaraldehyde, or any other bifunctional crosslinking agent.

Another very important characteristic of the invention is that the autopolymerized product is capable, after elimination of any excess glutaraldehyde, and having been placed in suspension in an aqueous medium, of gradually releasing the active agent in a soluble form, preserving the latter's antitumor activity. Thus, the active cytostatic agent is gradually released when the insoluble product is placed in a physiological solution, as is the case in therapeutic application. The reaction conditions mentioned above make it possible not to inhibit the therapeutic effect and, on the contrary, to increase the effectiveness of use of the antitumor agents.

The fixation of glutaraldehyde on the antitumor agent can be carried out directly or indirectly. The simplest means consists in placing the antitumor agent to be treated with the appropriate quantity of glutaraldehyde, particularly at ambient temperature, and in continuing the reaction until the insoluble product is formed and until there is no more, or substantially no more unreacted antitumor agent to be detected.

In an alternative manner, the glutaraldehyde can also be first fixed on a carrier and the combination is then reacted with an antitumor agent. For the purpose of the invention, cells and more particularly lymphocytes, are preferably employed as carriers. This fixation technique is described, in particular, in French Patent Application No. 80/06,537 of Mar. 24, 1980 in the name of the present Applicant under the title "Cellular preparations applicable in human therapy, process of preparation and applications". Reference can also be made to Swiss Patent Application No. 5,429/80 of July 15, 1980, corresponding to the abovementioned French patent application. Other details relating to this technique are found in the publication by E. H. Relyveld and S. Ben-Efraim— Preparation of Highly Immunogenic Protein Conjugates by Direct Coupling to Glutaraldehyde-Treated Cells: Comparison with Commonly Used Preparations, J. Immunol. Methods 1981, 40, 209–217. These cell preparations consist of cells on which are fixed, at their surface, substances having a pharmacological activity. As cells, use is made preferably of normal or leukaemic lymphocytes. The fixation is carried out in the presence of a crosslinking agent, which is preferably glutaraldehyde.

According to this alternative form of embodiment of the invention, the insoluble product is in the form of a cell preparation, preferably lymphocyte-based, carrying the antitumor agent in the coupled form. In the same manner as in the case of a direct fixation of glutaraldehyde to the antitumor agent, the insoluble product obtained according to the said alternative form, can, when placed in suspension in an aqueous medium in the absence of glutaraldehyde, as can be the case in the organism, for example, gradually release the antitumor agent while preserving its cytostatic activity.

The experiments reported below relate to daunorubicin. The results obtained according to conventional protocols for measuring the therapeutic effect of daunorubicin have shown that the daunorubicin-based products of the invention are more toxic than free daunorubicin. However, they permit substantially equivalent therapeutic results to be obtained with smaller quantities, for example on the order of half of the corresponding quantities of free daunorubicin. The therapeutic effect of polymerized daunorubicin is also better when compared to the same quantity of the medication injected by successive dosages, as is the case in normal treatment, or in one single dose. The "delay" effect provided by the products of the invention therefore makes it possible to improve very appreciably the conditions of the treatment and, in particular, the comfort of the patient.

The products of the invention have the same applications as the antitumor agents from which they are derived. They are suitable for all the forms of use of such tumor agents, for example the injection of the cytotoxic derivative in situ, particularly into solid tumors, as well as in the treatments referred to at the beginning of the present description, involving chemoembolization or implantable pumps.

In the following examples, the invention is illustrated with daunorubicin (or its hydrochloride) as the antitumor agent.

EXAMPLE 1

Preparation of a polymeric product by reaction of glutaraldehyde with daunorubicin 1 mg/ml of daunorubicin (hydrochloride) in an aqueous solution is contacted at ambient temperature with glutaraldehyde at various concentrations, namely 0.027%, 0.27% and 2.7% by weight respectively, for 15 min. or 30 min. The results are collected together in Table 1.

The results of Table 1 show that the glutaraldehyde concentration of 0.27% by weight is the only one of the three concentrations tried which is suitable, according to the invention, for obtaining practically 100% of insoluble polymeric product.

EXAMPLE 2

Fixation of daunorubicin on cells

Coupling of daunorubicin (hydrochloride) on leukaemic cells L 1210 of the mouse C57 BL/6 XDBA/2 $F_1$ has been carried out. The reaction conditions and the results obtained are collected together in Table 2. It is found that daunorubicin is fixed on the cells and polymerizes.

The results in Table 2 demonstrate again the importance of the concentration of glutaraldehyde. With $2\times 10^7$/ml of cells and 1 mg/ml of daunorubicin, no fixed polymer is obtained at a concentration of 0.027% whatever the length of reaction, whilst a concentration of 0.27% produces a polymer. Similarly, a concentration of 0.108% of glutaraldehyde with $8\times 10^7$ cells/ml and 1 mg/ml of daunorubicin does not produce precipitated product, if the reaction of glutaraldehyde is inhibited by a rapid dilution after the contact period.

In the following description, there are given, collected together in Tables 3 to 7 below, the results obtained in pharmacological trials making it possible to measure the comparative toxicity and the antitumor activity of free daunorubicin, of polymeric daunorubicin (product of the invention obtained by direct treatment of daunorubicin with glutaraldehyde) and of daunorubicin grafted in a polymeric form (product of the invention obtained by preliminary fixation of daunorubicin on L 1210 cells and polymerization). The test conditions are shown in the Tables, with the results and comments.

The products under trial are injected by i.p. route into mice.

For the tests reported in Table 4, polymeric daunorubicin was prepared according to Example 1 from a quantity of 1 mg/ml of daunorubicin and a glutaraldehyde concentration of 0.27% by weight. The treatment conditions were as follows:

free daunorubicin: 1 injection of 1 mg/kg on days D 1.2.3.4. once daily polymeric daunorubicin: 1 injection of 1 mg/kg on days D 1.2.3.4., once daily polymeric daunorubicin: 1 injection of 4 mg/kg on D 1. On day D 0 the mice were inoculated with $10^5$ of leukaemic cells L 1210.

The same applies to Table 5, in which the treatments were as follows:

free daunorubicin: 1 mg/kg D 1.2.3.4.

polymeric daunorubicin:
 1 mg/kg D 1.4.7.
 0.25 mg/kg D 1.3.5.7.9.
 0.25 mg/kg D 1.2.3.4.

Table 6 gives a comparison of the results obtained for the following treatments, after an injection of $10^5$ leukaemic cells on D 0:

free daunorubicin 1 mg/kg D 1.2.3.4.
polymeric daunorubicin 0.5 mg/kg D 1.2.3.4.
polymeric daunorubicin 4 mg/ D 1.
grafted polymeric daunorubicin 0.5 mg/kg D 1.2.3.4.

Table 7 shows a comparison of the results of chemotherapy treatments in the following cases:

control test injection of $10^5$ leukaemic cells on D 0
 controls
 free daunorubicin 1 mg/kg D 1.2.3.4.
 free daunorubicin 4 mg/kg D 1.
 polymeric daunorubicin 4 mg/kg D 1.

The results of Tables 3 to 7 show that, in general, the antitumor agents according to the invention consisting of polymeric daunorubicin, whether grafted or not, are more toxic than free daunorubicin. In the chemotherapy treatment, however, results which are equivalent to those of free daunorubicin are obtained by using a quantity which is four times smaller of polymeric daunorubicin, whether grafted or not, or by injecting in a single dose a quantity equal to the free daunorubicin injected successively (4 mg/kg on day 1, instead of 1 mg/kg on days 1.2.3.4.). The treatment with the polymeric daunorubicin produces a number of surviving mice which is at least equal to that obtained with free daunorubicin. The effectiveness of use of daunorubicin is therefore clearly improved by the invention.

Needless to say, the invention is not limited to the preceding examples, which relate to daunorubicin (hydrochloride). The invention can, in fact, be applied in a general manner to all the antitumor agents carrying groups capable of reacting with bifunctional crosslinking agents and particularly with glutaraldehyde. Similarly, the grafting of polymeric product is not limited to the normal or leukaemic lymphocytes. Various cell preparations can, in fact, be employed according to the teaching of the abovementioned French Patent Application No. 80/06,537.

Other studies have also been carried out on the delay activity of daunorubicin treated according to the invention (or polymeric daunorubicin). The tests were carried out as above on experimental leukaemia L 1210 in mice.

The following protocol was applied:

Test 1—control 1: graft of $1 \times 10^5$ L 1210 cells by i.p. route Day 5 ($D_5$)

Test 2—control 2: graft L 1210, $D_5$; daunorubicin monomer 2 mg/kg, $D_6$

Test 3—control 3: graft L 1210, $D_5$; polymeric daunorubicin 2 mg/kg, $D_6$

Test 4—daunorubicin monomer 2 mg/kg, $D_3$; graft L 1210, $D_5$

Test 5—polymeric daunorubicin 2 mg/kg, $D_3$; graft L 1210, $D_5$

The results obtained after the above tests have been collected together in Table 8 below. The data in Table 8 show that the therapeutic effects of daunorubicin monomer (DM) and the polymer (DP), administered after the tumor graft, are substantially identical (tests 2 and 3). The delay effect of polymeric daunorubicin is highly significant; the therapeutic activity is increased under the conditions where the monomeric product has no effect (compare tests 4 and 5). The therapeutic activity is the same in tests 3 and 5.

TABLE 1

| Time of contact with glutaraldehyde | Glutaraldehyde concentration % | Quantity polymerized % | % daunorubicin released | | | | | |
|---|---|---|---|---|---|---|---|---|
| | | | 2 hrs. at ambient temperature | +2 hrs 37° C. | +2 hrs 37° C. | +2 hrs 37° C. | +2 hrs 37° C. | +1 night at +4° C. |
| 15 min | 0.027 | 68.75 | 10.9 | 6.5 | 4.9 | 3.8 | 3 | 8.1 |
| | 0.27 | 97.4 | 7.2 | 7.3 | 8.6 | 4.9 | 4.1 | 11.3 |
| | 2.7 | 57.4 | 6.5 | 7.8 | 5.2 | 5.2 | 3.9 | 6.9 |
| 30 min | 0.027 | 80 | 9.4 | 7 | 5.1 | 4.2 | 3.75 | 10.25 |
| | 0.27 | 97.4 | 4.6 | 5 | 5 | 4.6 | 4.6 | 18.5 |
| | 2.7 | 73.5 | 5.6 | 4.5 | 4.6 | 5.6 | 3.9 | 10.6 |

TABLE 2

| Glutaraldehyde concentration | Cell concentration | Daunorubicin concentration | Time of preliminary contact with cells | Total contact time | Cell appearance under the microscope | % Daunorubicin fixed on the cell walls and polymerized |
|---|---|---|---|---|---|---|
| 0.27% | $2 \times 10^7$/ml | 1 mg/ml | 0 | 15 min | colorless cells presence of polymerized daunorubicin | |
| 0.027% | $2 \times 10^7$/ml | 1 mg/ml | 0 | 15 min | orange cells + no polymer | |
| | | | 5 min | 15 min | orange cells ++ no polymer | |
| | | | 10 min | 15 min | orange cells +++ no polymer | |
| 0.027% | $2 \times 10^7$/ml | 0.5 mg/ml | 0 | 15 min | some stained cells | |
| | | 0.250 mg/ml | 0 | 15 min | | |
| | | 0.125 mg/ml | 0 | 15 min | | |
| 0.0027% | $2 \times 10^7$/ml | 1 mg/ml | 0 | 15 min | cells not stained | |
| | | | 5 min | 15 min | | |
| | | | 15 min | 15 min | | |
| 0.027% | $2 \times 10^7$/ml | 1 mg/ml | 5 min | 15 min | — | 59.4 |
| 0.054% | $2 \times 10^7$/ml | 1 mg/ml | 5 min | 15 min | — | 81.8 |
| 0.108% | $2 \times 10^7$/ml | 1 mg/ml | 5 min | 15 min | | 84.8 |
| 0.108% | $2 \times 10^7$/ml | 1 mg/ml | 5 min | 15 min | | |
| 0.027% | $8 \times 10^7$/ml | 1 mg/ml | 0 | 15 min | some stained cells | |
| | | | 5 min | 15 min | some stained cells | |
| | | | 10 min | 15 min | some stained cells | 37.4 |
| 0.054% | $8 \times 10^7$/ml | 1 mg/ml | 0 | 15 min | some stained cells | |
| | | | 5 min | 15 min | well stained cells | 68.8 |
| | | | 10 min | 15 min | weakly stained cells | 47.5 |
| 0.108% | $8 \times 10^7$/ml | 1 mg/ml | 0 | 15 min | some stained cells | |
| | | | 5 min | 15 min | well-stained cells | 87 |
| | | | 10 min | 15 min | well-stained cells | 80.3 |
| 0.108% | $8 \times 10^7$/ml | 1 mg/ml | 5 min | 15 min | | 84.8 |
| 0.216% | $8 \times 10^7$/ml | 1 mg/ml | 5 min | 15 min | | 80.5 |
| 0.432 | $8 \times 10^7$/ml | 1 mg/ml | 5 min | 15 min | | 86.5 |
| 0.108% | $8 \times 10^7$/ml | 1 mg/ml | 5 min | 15 min | | 64.4 |

TABLE 3

Toxicity of free daunorubicin polymeric daunorubicin grafted polymeric daunorubicin

| | injected (mg/kg) | Injections and comments | | | | Comments | | | | | | | | |
|---|---|---|---|---|---|---|---|---|---|---|---|---|---|---|
| | | D.1 | D.2 | D.3 | D.4 | D.5 | D.6 | D.7 | D.8 | D.10 | D.12 | D.13 | D.14 | MTS* |
| Free daunoru- | 1 | 1st inj. | 2nd inj. NAD | 3rd inj. NAD | 4th inj. NAD | — | — | — | — | — | — | — | — | all sur- |

TABLE 3-continued

Toxicity of free daunorubicin polymeric daunorubicin grafted polymeric daunorubicin

| | injected (mg/kg) | Injections and comments | | | | Comments | | | | | | | | |
|---|---|---|---|---|---|---|---|---|---|---|---|---|---|---|
| | | D.1 | D.2 | D.3 | D.4 | D.5 | D.6 | D.7 | D.8 | D.10 | D.12 | D.13 | D.14 | MTS* |
| bicin | | | | | | | | | | | | | | surviving |
| | 3 | 1st inj. | 2nd inj. NAD | 3rd inj. 1 = thin 2 = diarrhoea rest NAD | 4th inj. 1 = thin 2 = diarrhoea rest NAD | — | — | 1M ** | — | 2M | 2M | 4M | 1M | 10.7 |
| | 9 | 1st inj. | 2nd inj. (sick diarrhoea±) | 3rd inj. more diarrhoea thin | 3rd inj. diarrhoea finished thin | — | 2M | 3M | 5M | — | — | — | — | 6.3 |
| Grafted polymeric daunorubicin | 1 | 1st inj. | 2nd inj. NAD | 3rd inj. 1 = diarrhoea rest NAD | 4th inj. NAD | — | — | — | — | — | | | | all surviving |
| | 3 | 1st inj. | 2nd inj. NAD | 3rd inj. (diarrhoea) | 4th inj. sick- thin diarrhoea | — | — | 2M | 8M | — | | | | 6.8 |
| | 9 | 1st inj. | 2nd inj. (sick diarrhoea++) | no 3rd inj. diarrhoea+++ very sick | (9 mice) 3rd inj. 1M | — | 8M | — | — | — | | | | 4.8 |
| Polymeric daunorubicin | 1 | 1st inj. | 2nd inj. NAD | 3rd inj. NAD | 4th inj. 1 = thin diarrhoea | — | 1M | — | — | — | — | — | — | 9 survivors |
| | 3 | 1st inj. | 2nd inj. NAD | 3rd inj. 2 = thin diarrhoea | 4th inj. 1M sick thin | — | 1M | 4M | 1M | — | — | — | — | 6.75 (1 survivor) |
| | 9 | 1st inj. | 2nd inj. (sick diarrhoea+) | no 3rd inj. diarrhoea+++ very sick | 3rd inj. thin diarrhoea | 1M | 3M | 4M | 1M | — | — | — | — | 5.55 (1 survivor) |

*mean time of survival
**M = death

TABLE 4

| | mice surviving after the test | | | | | | | | | | | | | | | | |
|---|---|---|---|---|---|---|---|---|---|---|---|---|---|---|---|---|---|
| Preparations | 8th day | 9th day | 10th day | 12th | 13 | 14 | 15 | 17 | 19 | 20 | 21 | 24 | 26 | 27 | >60 (33) | MTS | ILS* % |
| Controls | 10/10 | 10/10 | 10/10 | 7/10 | 6/10 | 3/10 | 1/10 | 0/10 | — | — | — | — | — | — | — | 12.8 | |
| Free daunorubicin 1 mg/kg .1.2.3.4. | | | | | | | | 10/10 | 8/10 | 8/10 | 6/10 | 6/10 | 6/10 | 6/10 | 6 recovered | 19 (4 mice) | 40.6 |
| Polymeric daunorubicin 1 mg/kg D.1.2.3.4. | 9/10 | 7/10 | 6/10 | 4/10 | 4/10 | 4/10 | 4/10 | 3/10 | 3/10 | 2/10 | 2/10 | 2/10 | 2/10 | 1/10 | 1 recovered | 12,8 (9 mice) | 0 |
| Polymeric daunorubicin 4 mg/kg D.1 | | | | | | | | 10/10 | 8/10 | 8/10 | 8/10 | 7/10 | 6/10 | 6/10 | 6 recovered | 21 (4 mice) | 64 |

*% increased length of survival

TABLE 5

| | Mice surviving after the test | | | | | | | | | | | | | | |
|---|---|---|---|---|---|---|---|---|---|---|---|---|---|---|---|
| Days | 5 | 10 | 11 | 14 | 15 | 16 | 17 | 18 | 19 | 23 | 27 | 32 | 56 | MTS | ILS % |
| Controls | 8/10 | 7/10 | 1/10 | 1/10 | 0/10 | — | — | — | — | — | — | — | — | 9.1 | — |
| Free daunorubicin 1 mg/kg D.1.2.3.4. | 10/10 | 10/10 | 10/10 | 9/10 | 8/10 | 6/10 | 4/10 | 3/10 | 3/10 | 3/10 | 3/10 | 3/10 | 30% recovered | 15.4 | 69.2 |
| Polymeric | 9/10 | 9/10 | 9/10 | 9/10 | 6/10 | 6/10 | 4/10 | 3/10 | 2/10 | 2/10 | 2/10 | 1/10 | 10% | 12.9 | 41.7 |

TABLE 5-continued

| Days | Mice surviving after the test | | | | | | | | | | | | MTS | ILS % |
|---|---|---|---|---|---|---|---|---|---|---|---|---|---|---|
| | 5 | 10 | 11 | 14 | 15 | 16 | 17 | 18 | 19 | 23 | 27 | 32 | 56 | | |
| daunorubicin 1 mg/kg D.1.4.7. | | | | | | | | | | | | | recovered | | |
| Polymeric daunorubicin 0.25 mg/kg D.1.2.3.4. | 10/10 | 10/10 | 10/10 | 10/10 | 6/10 | 5/10 | 4/10 | 4/10 | 3/10 | 2/10 | 2/10 | 2/10 | 20% recovered | 15.5 | 70.3 |
| Polymeric daunorubicin 0.25 mg/kg D.1.3.5.7.9. | 10/10 | 10/10 | 10/10 | 10/10 | 9/10 | 6/10 | 4/10 | 1/10 | 1/10 | 1/10 | 0/10 | — | — | 16.8 | 84.6 |

TABLE 6

| Total mg | | Survivors after the test | | | | | | | | | |
|---|---|---|---|---|---|---|---|---|---|---|---|
| | | D.4 | 5 | 10 | 11 | 12 | 13 | 14 | 15 | 16 | 17 |
| 0 | Controls test | 10/10 | 10/10 | 8/10 | 6/10 | 4/10 | 0/10 | — | — | — | — |
| 4 | Controls free daunorubicin 1 mg/kg D.1.2.3.4. | 9/10 .1.2.3.4. | 9/10 | 9/10 | 9/10 | 9/10 | 9/10 | 9/10 | 7/10 | 3/10 | 3/10 |
| 2 | Polymeric daunorubicin 0.5 mg/kg D.1.2.3.4. | 10/10 | 10/10 | 10/10 | 9/10 | 9/10 | 9/10 | 7/10 | 7/10 | 5/10 | 5/10 |
| 4 | Polymeric daunorubicin 4 mg/kg D.1. | 10/10 | 10/10 | 10/10 | 10/10 | 9/10 | 9/10 | 8/10 | 8/10 | 6/10 | 4/10 |
| 2 | Grafted daunorubicin 0.5 mg/kg D.1.2.3.4. | 10/10 | 9/10 | 9/10 | | 9/10 | 8/10 | 7/10 | 7/10 | 6/10 | 4/10 |

| Total mg | | Survivors after the test | | | | | | | | | MTS | ILS % |
|---|---|---|---|---|---|---|---|---|---|---|---|---|
| | | 18 | 19 | 21 | 22 | 23 | 24 | 25 | 44 | 66 | | |
| 0 | Controls test | — | — | — | — | — | — | — | — | — | 10.8 | — |
| 4 | Controls free daunorubicin 1 mg/kg D.1.2.3.4. | 3/10 | 3/10 | 2/10 | 2/10 | 2/10 | 2/10 | 2/10 | 2/10 | 2/10 | 13.2 | 22.2 |
| 2 | Polymeric daunorubicin 0.5 mg/kg D.1.2.3.4. | 4/10 | 3/10 | 3/10 | 2/10 | 1/10 | 1/10 | 1/10 | 1/10 | 1/10 | 16 | 48.1 |
| 4 | Polymeric daunorubicin 4 mg/kg D.1. | 3/10 | 3/10 | 3/10 | 3/10 | 3/10 | 3/10 | 3/10 | 2/10 | 2/10 | 18.25 | 69 |
| 2 | Grafted daunorubicin 0.5 mg/kg D.1.2.3.4. | 4/10 | 4/10 | 4/10 | 2/10 | 2/10 | 1/10 | 0/10 | — | — | 17.9 | 65.7 |

TABLE 7

| | 11 | 12 | 13 | 14 | 15 | 16 | 17 | 18 | 19 | 20 | 21 | 22 | 23 | 27 | MTS | ILS % |
|---|---|---|---|---|---|---|---|---|---|---|---|---|---|---|---|---|
| Controls test | 4/10 | 1/10 | 0/10 | — | — | — | — | — | — | — | — | — | — | — | 10.5 | |
| Free daunorubicin 1 mg/kg D.1.2.3.4. | | | 10/10 | 9/10 | 9/10 | 8/10 | 7/10 | 5/10 | 5/10 | 5/10 | 3/10 | 1/10 | 0/10 | — | 18.2 | 73.3 |
| Polymeric daunorubicin 4 mg/kg D.1. | | | 10/10 | 9/10 | 8/10 | 8/10 | 6/10 | 5/10 | 4/10 | 3/10 | 3/10 | 2/10 | 1/10 | — | 20.6 | 96.2 |
| Free daunorubicin 4 mg/kg D.1 | | | | 10/10 | 8/10 | 4/10 | 2/10 | 0/10 | — | — | — | — | — | — | 16.4 | 58.2 |

TABLE 8

| | Number of mice surviving after the test | | | | | | | | | | | | | MTS | ILS |
|---|---|---|---|---|---|---|---|---|---|---|---|---|---|---|---|
| | D 9 | 10 | 11 | 12 | 13 | 14 | 15 | 16 | 17 | 18 | 19 | 20 | 21 | 27 | ±SD | % |
| Test 1 | 10/10 | 7/10 | 4/10 | 2/10 | 0/10 | — | — | — | — | — | — | — | — | — | 10.5 ± 1.5 | — |
| Test 2 | | | | 10/10 | 9/10 | 9/10 | 9/10 | 8/10 | 6/10 | 2/10 | 0/10 | — | — | — | 16.3 ± 1.8 | 55.2 |
| Test 3 | | | 10/10 | 9/10 | 9/10 | 9/10 | 9/10 | 9/10 | 7/10 | 5/10 | 4/10 | 1/10 | 0/10 | — | 17.2 ± 2.6 | 63.8 |
| Test 4 | 8/10 | 8/10 | 5/10 | 4/10 | 3/10 | 0/10 | — | — | — | — | — | — | — | — | 10.8 ± 1.9 | 2.8 |
| Test 5 | | | | | | 10/10 | 9/10 | 8/10 | 5/10 | 4/10 | 4/10 | 2/10 | 1/10 | 0/10 | 17.8 ± 3.45 | 69.5 |

What is claimed is:

1. Autopolymerized antitumor agent, comprising the product of the reaction of an active antitumor agent which is daunorubicin or a pharmaceutically acceptable acid addition salt thereof, with an autopolymerizing-effective amount of glutaraldehyde to provide a product which is insoluble in aqueous medium, but which provides timed release of the active antitumor agent when suspended in aqueous medium.

* * * * *